(12) United States Patent
Xing

(10) Patent No.: US 10,518,456 B2
(45) Date of Patent: Dec. 31, 2019

(54) METHOD FOR PREPARING PBAT LAMINATED MEMBRANE COMPOSITE MATERIAL AND USES

(71) Applicant: SHANDONG BENEFIT NEW MATERIAL CO., LTD., Yantai, Shandong (CN)

(72) Inventor: Peng Xing, Shandong (CN)

(73) Assignee: SHANDONG BENEFIT NEW MATERIAL CO. LTD., Yantai, Shandong (CN)

( * ) Notice: Subject to any disclaimer, the term of this patent is extended or adjusted under 35 U.S.C. 154(b) by 0 days.

(21) Appl. No.: 15/550,009

(22) PCT Filed: Jul. 23, 2015

(86) PCT No.: PCT/CN2015/084903
§ 371 (c)(1),
(2) Date: Aug. 9, 2017

(87) PCT Pub. No.: WO2016/127586
PCT Pub. Date: Aug. 18, 2016

(65) Prior Publication Data
US 2018/0023181 A1    Jan. 25, 2018

(30) Foreign Application Priority Data

Feb. 9, 2015 (CN) .......................... 2015 1 0066772
Jun. 17, 2015 (CN) .......................... 2015 1 0337604

(51) Int. Cl.
*B29C 48/00* (2019.01)
*B29C 35/00* (2006.01)
(Continued)

(52) U.S. Cl.
CPC ............ *B29C 48/022* (2019.02); *A61L 15/18* (2013.01); *A61L 15/225* (2013.01); *A61L 15/26* (2013.01);
(Continued)

(58) Field of Classification Search
CPC ........ C23C 14/02; A61L 15/225; A61L 15/42; A61L 15/18; A61L 15/26; A61L 2420/04;
(Continued)

(56) References Cited

U.S. PATENT DOCUMENTS

| 6,025,028 | A | * | 2/2000 | Asrar | ............. | C09D 167/04 |
| | | | | | | 427/358 |
| 2012/0015176 | A1 | * | 1/2012 | Riebel | ............. | B32B 27/06 |
| | | | | | | 428/323 |
| 2014/0162004 | A1 | * | 6/2014 | Moore | ............. | C08J 7/047 |
| | | | | | | 428/35.7 |

OTHER PUBLICATIONS

Chen et al., "Preparation and characterization of nanocomposite of maleated poly(butylene adipate-co-terephthalate) with organoclay," Materials Science and Engineering C 46 (2015) 301-308. (Year: 2015).*

* cited by examiner

*Primary Examiner* — William P Fletcher, III
(74) *Attorney, Agent, or Firm* — Liang Legal Group, PLLC

(57) ABSTRACT

A method for preparing a PBAT laminated membrane composite material uses PBAT or a material with PBAT as the main component and other biodegradable plastic or superfine calcium carbonate in a mixture. The temperature of the mixture is increased by means of a lamination machine segment by segment, the material is heated slowly to a molten state, and the temperature of a rolling shaft is controlled by introducing cold water to the rolling shaft when the lamination machine conducts membrane lamination, so that the temperatures of rolling wheels and the laminated membrane are controlled.

10 Claims, 1 Drawing Sheet

(51) Int. Cl.
  *B29C 48/285* (2019.01)
  *B29C 48/80* (2019.01)
  *B29C 48/08* (2019.01)
  *B29C 48/355* (2019.01)
  *B29C 48/88* (2019.01)
  *B29C 31/02* (2006.01)
  *B29C 41/08* (2006.01)
  *C08K 3/26* (2006.01)
  *C08L 67/02* (2006.01)
  *A61L 15/18* (2006.01)
  *A61L 15/22* (2006.01)
  *A61L 15/26* (2006.01)
  *A61L 15/42* (2006.01)
  *C09D 167/02* (2006.01)
  *A61L 15/50* (2006.01)
  *B05D 7/24* (2006.01)
  *B05D 1/26* (2006.01)
  *B05D 3/00* (2006.01)

(52) U.S. Cl.
  CPC .............. *A61L 15/42* (2013.01); *A61L 15/50* (2013.01); *B05D 1/265* (2013.01); *B05D 3/007* (2013.01); *B05D 7/24* (2013.01); *B29C 31/02* (2013.01); *B29C 35/00* (2013.01); *B29C 41/08* (2013.01); *B29C 48/08* (2019.02); *B29C 48/285* (2019.02); *B29C 48/286* (2019.02); *B29C 48/355* (2019.02); *B29C 48/80* (2019.02); *B29C 48/802* (2019.02); *B29C 48/911* (2019.02); *B29C 48/914* (2019.02); *B29C 48/9135* (2019.02); *C08K 3/26* (2013.01); *C08L 67/02* (2013.01); *C09D 167/02* (2013.01); *A61L 2420/04* (2013.01); *A61L 2420/06* (2013.01); *B05D 2203/22* (2013.01); *B05D 2252/02* (2013.01); *C08K 2003/265* (2013.01); *C08K 2201/018* (2013.01)

(58) Field of Classification Search
  CPC ... A61L 2420/06; A61L 15/50; C09D 167/02; C08K 3/26; C08K 2003/265; C08K 2201/018; B29C 41/08; B29C 31/02; B29C 35/00; B29C 48/00; B29C 48/022; B29C 48/08; B29C 48/285; B29C 48/286; B29C 48/355; B29C 48/80; B29C 48/802; B29C 48/911; B29C 48/9135; B29C 48/914; C08L 67/02; B05D 5/00; B05D 3/007; B05D 1/265; B05D 7/24; B05D 2252/02; B05D 2203/22
  See application file for complete search history.

METHOD FOR PREPARING PBAT LAMINATED MEMBRANE COMPOSITE MATERIAL AND USES

BACKGROUND OF THE INVENTION

Technical Field

The present invention relates to a preparation method of a degradable composite material and applications thereof, particularly to a preparation method of a composite material prepared by using a film coating technology and applications thereof, which belongs to the field of composites.

Description of Related Art

In order to prevent liquid to freely seep into paper materials, paper food containers, an anti-seeping, leak-proof, water-proof and humid-proof paper containers and garbage containers, paper diapers and sanitary towels are usually coated with a plastic film on the inner and outer surfaces to achieve the waterproof and leak-proof effects. Polyethylene (PE) or polypropylene (PP) is usually used as the raw materials during film coating. Paper tools coated with films have waterproof and leak-proof effects. However, PE and PP cannot be biologically degraded and generate a vast amount of white garbage, polluting environment.

In order to solve the problem of plastic pollution, a PLA (polylactic acid) coating paper has been developed in the industry. The PLA can be naturally degraded, and is non-toxic and environmentally-friendly, but the PLA is greatly limited in application scopes because of its disadvantages such as brittleness, toughness, impact resistance and thermal stability. Moreover, the current PLA coating technology has a certain limit in the thickness of coated film. The thickness of the PLA film cannot be smaller than 22 g/m$^2$, causing high cost to the PLA film. Another biologically degradable material PBS (poly(butylene succinate)) features low processing temperature, low viscosity and poor melting strength. In addition, PLA and PBS are crystalline polymers, and products thereof usually have a certain brittleness. Therefore, the PLA and PBS are greatly limited in the application scope in the packing field.

In the present invention, PBAT (poly(butylene adipate-co-terephthalate)) is a copolymer of butylene adipate and butylene terephthalate, which has outstanding ductility and elongation at breaking point and also has good heat resistance and impact resistance. Besides, PBAT is also an excellent biologically degradable material and therefore can be used to improve the mechanical properties of the fatty polyesters such as PLA. "The Study on Super-Fine Calcium Carbonate Filled Degradable Polyester Materials (Plastic, 2009, 38 (3): 69-71, Xiao Yunhe, et al.) shows that the mixing of the PBAT and the calcium carbonate will not only realize complete quick degradation of materials but also greatly save on costs. However, the PBAT has a physical feature of very high viscosity, the PBAT adheres very easily to the equipment during coating operations, causing failure to its continuous production. Therefore, the report of a successful use of the PBAT film is not seen yet.

SUMMARY OF THE INVENTION

Aiming at the problems in the PBAT film coating process, the present invention provides a preparation method of a PBAT film composite and applications.

The present invention adopts the following technical solutions to solve the technical problems.

A preparation method for a PBAT film composite, comprising the following steps:

I. putting PBAT or a mixture of 100 weight parts of PBAT and 5-40 weight parts of other biodegradable plastic or 5-40 weight parts of super-fine calcium carbonate, as a base stock, into a mixing tank, mixing, heating and drying the base stock;

II. conveying the base stock dried in step I to a storage bin of a coating machine by a raw materials conveyor;

III. sending the base stock in the storage bin in step II into the coating machine via a feed port, heating and pushing the base stock by a screw, wherein the coating machine is divided into a plurality of heating segments along the direction of the screw, and the temperature of the heating segments gradually rises to the melting point of the base stock along the direction of the screw, and sending the melt base stock to a coating tool of the coating machine via a material conveying elbow;

IV. pushing the coating machine table to a certain position by using advance guide wheels at the bottom of the coating machine table such that the coating tool of the coating machine as described in step III is positioned between two rollers of the coating machine table, turning the coating tool by a fixed sliding base which is driven by a transverse cylinder such that the coating tool is positioned on the central line between the two rollers of the coating machine table, finally raising the coating machine table under the control of a pushing oil hydraulic cylinder such that the coating central line between the two rollers keeps a certain distance away from a discharge opening of the coating tool;

V. conveying a substrate to a position between the two rollers of the coating machine table by a substrate shaft, controlling the coating machine to cover a base stock film on the substrate, controlling the complexing strength between the base stock and the substrate by controlling the pressure between the two rollers through a transverse air cylinder, wherein the substrate is any one of paper, non-woven fabric or thin paperboard; pumping cooling water into the rollers to control the temperature of the rollers to be 20-30° C., thus ensuring that the melt film is capable of being quickly cooled and solidified after being covered on the substrate, complexing the film on the substrate and separating the film from the rollers.

The present invention has the following beneficial effects:

By the method, the PBAT and the biological degradable mixture which takes the PBAT as the main component can be successfully compounded on a substrate by means of coating, and the obtained composite, compared with the PLA film coated, has an excellent mechanical property and can present equivalent or better waterproof, oil-proof and temperature-resistant qualities and the thickness of the PBAT film is in a large scope, and the minimum thickness reaches 10 g/m2, greatly reducing the cost of the composite.

Based on the above technical solution, the present invention can be improved in the following way.

Further, in step V water sprayers on the upper parts of the rollers are started to spray 10-20° C. water while the cooling water is pumped into the roller shafts.

By adopting the above further technical solution, the present invention has the beneficial effect that the base stock film can be quickly cooled and solidified after being coated on the substrate and separated from the rollers.

Further, the rollers are made of an anti-adhesive material.

By adopting the above further technical solution, the present invention has the beneficial effect that the base stock film coated on the substrate can be very easily separated from the rollers, realizing continuous production.

Further, the anti-adhesive material is selected from any one of polytetrafluoroethylene, ceramic and fluorocarbon rubber modified silica gel.

Further, the other biodegradable plastic in step I refer to any one or mixture of PLA and PBS.

Further, the number of the heating segments in step III is six.

Further, the heating temperature of the six heating segments gradually increases by 30-40° C., 60-70° C., 10-20° C., 10-20° C. and 10-20° C. on the basis of 150° C.

Further, the pre-set distance from the central line between the two rollers (10) to the discharge opening of the coating tool (7) in step IV is 3-7 cm.

Further, the pressure between the two rollers (10) in step V is controlled at 0.5-0.8 Mpa.

The present invention also provides applications of the preparation method of the PBAT film composite in the fields of degradable paper diapers, sanitary towels and packings.

BRIEF DESCRIPTION OF THE SEVERAL VIEWS OF THE DRAWINGS

As shown in FIG. 1 and FIG. 2, 1. mixing tank; 2. raw materials conveyor; 3. storage bin; 4. feed port; 5. screw conveyor; 6. conveying elbow; 7. coating tool; 8. water sprayer; 9. film; 10. roller; 11. transverse air cylinder; 12. fixed sliding base; 13. substrate shaft; 14. winding machine; 15. coating machine table; 16. table advance guide wheel; 18. table advance guide rail; 19. pushing oil cylinder.

DETAILED DESCRIPTION OF THE INVENTION

The principle and characteristic of the present invention are described in conjunction with the embodiments. The embodiments listed are used for explaining the present invention, not limiting the scope of the present invention.

Embodiment 1

Figure 1:
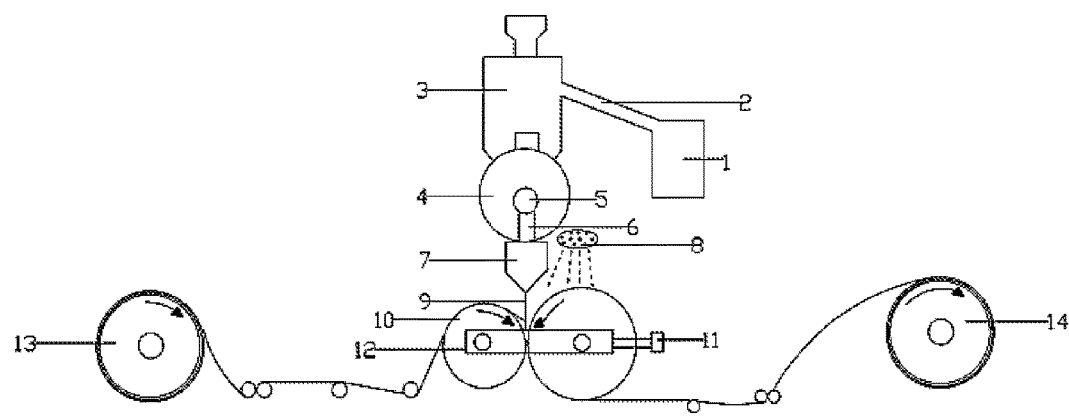
FIG. 1 is a schematic view of a whole coating production line of the present invention.
Figure 2:
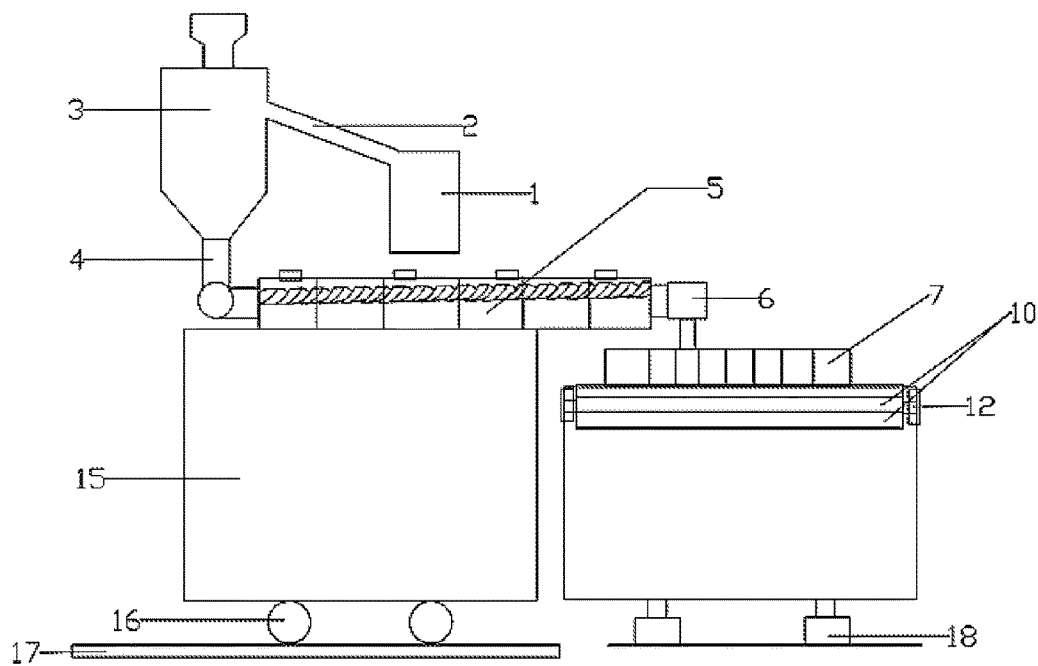
FIG. 2 is a side view of a coating machine in the present invention.

As shown in FIG. 1 and FIG. 2, a device for preparing a PBAT film composite includes a mixing tank 1, a raw materials conveyor 2 and a coating machine; the mixing tank 1 is connected with the feed port 4 of a coating machine via a raw materials conveyor 2; and water sprayers 8 are installed on the upper parts of two rollers 10.

1,000 g of PBAT is added into and dried in the mixing tank 1. The revolving speed of the mixing tank is 500 r/min. After being dried for 5 min, the PBAT is conveyed to the storage bin 3 of the coating machine by the raw material conveyor 2. The PBAT enters the screw conveyor 5 of the coating machine via the feed port 4. The screw is divided into six heating segments of which the temperature is respectively set as 150° C., 190° C., 260° C., 275° C., 285° C. and 305° C. in turn. The melt PBAT reaches a coating tool 7 of the coating machine. The coating machine is pushed to a certain position by the advance guide wheels 16 at the bottom of the coating machine table such that the coating tool 7 of the coating machine is positioned between two rollers 10. Then, tuned by using a fixed sliding base 12 of the coating machine table, the coating tool 7 of the coating machine is positioned at the central line between the two rollers 10 of the roller table. Finally, the coating machine table is controlled to rise under the control of the pushing oil cylinder 18 such that the coating central line between the two rollers 10 is 4 cm away from the discharge opening of the coating tool 7. The coating machine is controlled to coat the PBAT on a piece of 40 m2 paper, and the pressure between two rollers is controlled to be 0.6 Mpa. Meanwhile, cooling water is pumped into roller shafts to control the temperature of the roller shafts to be 20° C. The water sprayers 8 spray 20° C. water onto the rollers 10 at the same time. Finally, the coating thickness of the obtained composite coating paper is 25 g/m2. The tensile test data of the composite coating paper can be seen in table 1.

Embodiment 2

By using the equipment identical with that in embodiment 1, 1,000 g of PBAT and 50 g of NatureWorks 4032D PLA are added into and dried in the mixing tank 1. The revolving speed of the mixing tank is 500 r/min. After being dried for 5 min, the PBAT and the PLA are conveyed to the storage bin 3 of the coating machine by the raw material conveyor 2. The PBAT and the PLA are heated and pushed by the screw conveyor of the coating machine. The screw is divided into six heating segments of which the temperature is respectively set as 160° C., 190° C., 260° C., 280° C., 290° C. and 315° C. in turn. The melted PBAT and the PLA reach the coating tool 7 of the coating machine. The coating machine table 15 is pushed to a certain position by the advance guide wheels 16 at the bottom of the coating machine table such that the coating tool 7 of the coating machine is positioned between two rollers 10. Then, turned by using a fixed sliding base 12 of the coating machine table, the coating tool 7 of the coating machine is positioned at the central line between the two rollers 10 of the roller table. Finally, the coating machine table is controlled to rise under the control of the pushing oil cylinder 18 such that the coating central line between the two rollers 10 is 7 cm away from the discharge opening of the coating tool 7. The coating machine is controlled to coat the PBAT on a piece of 100 m2 non-woven fabric, and the pressure between two rollers is controlled to be 0.5 Mpa. Meanwhile, cooling water is pumped into roller shafts to control the temperature of the roller shafts to be 25° C. The water sprayers 8 spray 10° C. water onto the rollers 10 at the same time. The coating thickness is 10.5 g/m2. The tensile test data of the composite coating material can be seen in table 1.

Embodiment 3

The equipment with a structure identical with that in embodiment 1 is used, and the rollers are made of polytetrafluor materials.

1,000 g of PBAT and 400 g of TH801T PBS produced by Xinjiang Blue Ridge Tunhe Chemical Industry Joint Stock Co., Ltd. are added into and dried in the mixing tank 1. The revolving speed of the mixing tank is 500 r/min. After being dried for 5 min, the PBAT and the PBS are conveyed to the storage bin 3 of the coating machine by the raw material conveyor 2. The PBAT and the PBS are heated and pushed by the screw conveyor of the coating machine. The screw is divided into six heating segments of which the temperature is respectively set at 150° C., 180° C., 270° C., 280° C., 290° C. and 300° C. in turn. The melt PBAT and the PBS reach the coating tool 7 of the coating machine. The coating machine table 15 is pushed to a certain position by the advance guide wheels 16 at the bottom of the coating machine table such that the coating tool 7 of the coating machine is positioned between two rollers 10. Then, tuned by using the fixed sliding base 12 of the coating machine table, the coating tool 7 of the coating machine is positioned at the central line between the two rollers 10 of the roller table. Finally, the coating machine table is controlled to rise under the control of the pushing oil cylinder 18 such that the coating central line between the two rollers 10 is 5 cm away from the discharge opening of the coating tool 7. The coating machine is controlled to coat the PBAT on a piece of 80 m2 paper, and the pressure between two rollers is controlled to be 0.5 Mpa. Meanwhile, cooling water is pumped into roller shafts to control the temperature of the roller shafts to be 25° C. The coating thickness is 17.5 g/m2. The tensile test data of the composite coating material can be seen in table 1.

Embodiment 4

The equipment with a structure identical with that in embodiment 1 is used, and the rollers are made of silicone carbide ceramic materials.

1,000 g of PBAT and 200 g of super-fine calcium carbonate are added into and dried in the mixing tank 1. The revolving speed of the mixing tank is 500 r/min. After being dried for 5 min, the PBAT and the super-fine calcium carbonate are conveyed to the storage bin 3 of the coating machine by the raw materials conveyor 2. The PBAT and the super-fine calcium carbonate are heated and pushed by the screw conveyor of the coating machine. The screw is divided into six heating segments of which the temperature is respectively set as 160° C., 190° C., 270° C., 300° C., 330° C. and 350° C. in turn. The melted PBAT and the super-fine calcium carbonate reach the coating tool 7 of the coating machine. The coating machine table 15 is pushed to a certain position by the advance guide wheels 16 at the bottom of the coating machine table such that the coating tool 7 of the coating machine is positioned between two rollers 10. Then, turned by using the fixed sliding base 12 of the coating machine table, the coating tool 7 of the coating machine is positioned at the central line between the two rollers 10 of the roller table. Finally, the coating machine table is controlled to rise under the control of the pushing oil cylinder 18 such that the coating central line between the two rollers 10 is 5 cm away from the discharge opening of the coating tool 7. The coating machine is controlled to coat the PBAT on a piece of 50 m2 thin paper board, and the pressure between two rollers is controlled to be 0.5 Mpa. Meanwhile, cooling water is pumped into the roller shafts to control the temperature of the roller shafts to be 25° C. The coating thickness is 24 g/m2. The tensile test data of the composite coating material can be seen in table 1.

Embodiment 5

The equipment with a structure identical with that in embodiment 1 is used, and the rollers are made of silica gel.

1,000 g of PBAT and 180 g of TH801T PBS produced by Xinjiang Blue Ridge Tunhe Chemical Industry Joint Stock Co., Ltd. are added into and dried in the mixing tank 1. The revolving speed of the mixing tank is 500 r/min. After being dried for 5 mins, the PBAT and the PBS are conveyed to the storage bin 3 of the coating machine by the raw materials conveyor 2. The PBAT and the PBS are heated and pushed by the screw conveyor of the coating machine. The screw is divided into six heating segments of which the temperature is respectively set as 150° C., 180° C., 270° C., 280° C., 290° C. and 300° C. in turn. The melted PBAT and the PBS reach the coating tool 7 of the coating machine. The coating machine table 15 is pushed to a certain position by the advance guide wheels 16 at the bottom of the coating machine table such that the coating tool 7 of the coating machine is positioned between two rollers 10. Then, turned by using the fixed sliding base 12 of the coating machine table, the coating tool 7 of the coating machine is positioned at the central line between the two rollers 10 of the roller table. Finally, the coating machine table is controlled to rise under the control of the pushing oil cylinder 18 such that the coating central line between the two rollers 10 is 5 cm away from the discharge opening of the coating tool 7. The coating machine is controlled to coat the PBAT on a piece of 100 m2 paper, and the pressure between two rollers is controlled to be 0.5 Mpa. Meanwhile, cooling water is pumped into the roller shafts to control the temperature of the roller shafts to be 25° C. The coating thickness is 11.8 g/m2. The tensile test data of the composite coating materials can be seen in table 1.

The experimental parameters of the tensile test in table 1 are as follows:

Test temperature: 0° C.; test speed: 100 mm/min; clamping length: 100 mm.

TABLE 1

Tensile test data of products obtained in embodiments 1-4

| Test object | Transverse tension 150 N | | Vertical tension 350 N | |
|---|---|---|---|---|
| | Elongation at break % | Break time/sec | Elongation at break % | Break time/sec |
| Embodiment 1 | 5.70 | 4.10 | 1.9 | 1.41 |
| Embodiment 2 | 6.10 | 4.46 | 1.9 | 1.45 |
| Embodiment 3 | 6.5 | 4.82 | 1.5 | 1.35 |
| Embodiment 4 | 4.8 | 4.25 | 1.7 | 1.40 |
| Embodiment 5 | 5.3 | 4.15 | 1.8 | 1.42 |

The above embodiments are only preferably embodiments of the present invention and shall not be regarded as a limit of the present invention. Any modifications, equivalent replacements and improvement made within the concept and principle of the present invention shall fall within the protective scope of the present invention.

What is claimed is:

1. A method for preparing a PBAT film composite, comprising the following steps of:
   I. putting PBAT or a mixture of 100 weight parts of PBAT and 5-40 weight parts of a biodegradable plastic or 5-40 weight parts of super-fine calcium carbonate, as a base stock, into a mixing tank (1), mixing, heating and drying the base stock;
   II. conveying the base stock dried in step I to a storage bin (3) of a coating machine by a raw material conveyor (2);
   III. sending the base stock in the storage bin (3) from step II into the coating machine via a feed port (4), heating and pushing the base stock using a screw (5), wherein the coating machine is divided into a plurality of heating segments along a direction of the screw (5), and temperatures of the heating segments gradually rise to the melting point of the base stock along the direction of the screw (5), and sending the melted base stock to a coating tool (7) of the coating machine via a material conveying elbow (6);
   VI. pushing a coating machine table (15) to a selected position using advance guide wheels (16) at a bottom of the coating machine table (15) such that the coating tool (7) as described in step III is positioned between two rollers (10) of the coating machine table (15), turning the coating tool (7) by a fixed sliding base (12) which is driven by a transverse cylinder (11) such that the coating tool (7) is positioned on a central line between the two rollers (10) of the coating machine table (15), finally raising the coating machine table (15) under control of a pushing oil hydraulic cylinder (18) such that the coating central line between the two rollers (10) keeps a selected distance away from a discharge opening of the coating tool (7);

V. conveying a substrate to a position between the two rollers (10) of the coating machine table (15) by a substrate shaft, controlling the coating machine to cover a base stock film on a substrate, controlling a complexing strength between the base stock and the substrate by controlling a pressure between the two rollers (10) through a transverse air cylinder (11), wherein the substrate is any one of paper, non-woven fabric or thin paperboard; pumping cooling water into the rollers to control a temperature of the rollers to be 20-30° C., thus ensuring that a melted film (9) is capable of being quickly cooled and solidified after being covered on the substrate, complexing the film (9) on the substrate and separating the film from the rollers (10).

2. The method according to claim 1, wherein in step V water sprayers (8) on the upper parts of the rollers start to spray 10-20° C. water while the cooling water is pumped into the roller shafts.

3. The method according to claim 1, wherein the rollers (10) are made of anti-adhesive materials.

4. The method according to claim 3, wherein the anti-adhesive materials are selected from any one of polytetrafluoroethylene, ceramic, and fluorocarbon rubber and modified silica gel.

5. The method according to claim 1, wherein the other biodegradable plastic in step I refers to any one or mixture of PLA and PBS.

6. The method according to claim 5, wherein the melting point of PLA is 155-170° C., and the melting point of PBS is 110-120° C.

7. The method according to claim 1, wherein the number of the heating segments in step III is 6.

8. The method according to claim 6, wherein the heating temperature of the six heating segments gradually increases by 30-40° C., 60-70° C., 10-20° C., 10-20° C. and 10-20° C. on the basis of 150° C.

9. The method according to claim 1, wherein the pre-set distance from the central line between the two rollers (10) to the discharge opening of the coating tool (7) in step IV is 3-7 cm.

10. The method according to claim 1, wherein the pressure between the two rollers (10) in step V is controlled to be 0.5-0.8Mpa.

* * * * *